(12) United States Patent
Eide (10) Patent No.: US 12,144,912 B2
(45) Date of Patent: Nov. 19, 2024

(54) PHOTOCATALYTIC OXIDATION DEVICE FOR TREATMENT OF AIR

(71) Applicant: AERUS, LLC, Dallas, TX (US)

(72) Inventor: Andrew Eide, Rockwall, TX (US)

(73) Assignee: AERUS, LLC, Dallas, TX (US)

( * ) Notice: Subject to any disclaimer, the term of this patent is extended or adjusted under 35 U.S.C. 154(b) by 385 days.

(21) Appl. No.: 16/985,443

(22) Filed: Aug. 5, 2020

(65) Prior Publication Data
US 2021/0038755 A1 Feb. 11, 2021

Related U.S. Application Data

(60) Provisional application No. 63/006,270, filed on Apr. 7, 2020, provisional application No. 62/883,410, filed on Aug. 6, 2019.

(51) Int. Cl.
*A61L 9/20* (2006.01)
*F24F 8/22* (2021.01)

(52) U.S. Cl.
CPC ........ *A61L 9/205* (2013.01); *B01D 2255/802* (2013.01); *F24F 8/22* (2021.01)

(58) Field of Classification Search
CPC ........ A61L 9/205; A61L 9/20; A61L 2209/12; F24F 3/16; F24F 8/22; B01D 2255/802; B01D 53/885; B01D 2259/804; B01D 2255/20707; B01D 2258/06; B01D 53/8668; B01D 53/007; B01D 2257/708; H01J 65/042; H01J 61/35; H01J 61/16; H01J 61/302; B82Y 20/00; C03C 2217/213; C03C 17/25
See application file for complete search history.

(56) References Cited

U.S. PATENT DOCUMENTS

| | | |
|---|---|---|
| 6,238,631 B1 | 5/2001 | Ogata et al. |
| 7,425,226 B2 | 9/2008 | Powell |
| 7,674,436 B1 | 3/2010 | Feldman et al. |
| 8,658,101 B1 | 2/2014 | Burnett |
| 9,011,780 B1 | 4/2015 | Burnett |
| 9,011,789 B2 | 4/2015 | Clausen et al. |
| 9,623,374 B2 | 4/2017 | Eide |

(Continued)

FOREIGN PATENT DOCUMENTS

| | | |
|---|---|---|
| CN | 105435627 A | 3/2016 |
| DE | 1965022 A1 | 7/1970 |

(Continued)

OTHER PUBLICATIONS

European Search Report and Search Opinion Received for EP Application No. 15891382.2, mailed on Dec. 20, 2018, 8 pages.

(Continued)

*Primary Examiner* — Xiuyu Tai
(74) *Attorney, Agent, or Firm* — Workman Nydegger (57) ABSTRACT

Disclosed herein is a photocatalytic oxidation device that includes a frame and a pair of opposing photocatalytic cell panels. An ultraviolet lamp is disposed within an interior chamber and, when activated, causes the generation of oxidizers at the cell panels. Air is passable through apertures of the cell panels and thus may be moved through the device. The device is structurally configured and dimensionally optimized to provide effective photocatalytic activity without overly restricting airflow.

14 Claims, 7 Drawing Sheets

(56) References Cited

U.S. PATENT DOCUMENTS

| | | | |
|---|---|---|---|
| 9,867,897 | B2 | 1/2018 | Eide |
| 2006/0057020 | A1 | 3/2006 | Tufo |
| 2006/0262389 | A1 | 11/2006 | Zaczek |
| 2009/0035176 | A1 | 2/2009 | Normark et al. |
| 2009/0041617 | A1 | 2/2009 | Lee |
| 2012/0000860 | A1 | 1/2012 | Arenshtam et al. |
| 2012/0315184 | A1 | 12/2012 | Clark |
| 2014/0050611 | A1 | 2/2014 | Warren et al. |
| 2014/0065023 | A1 | 3/2014 | Eide |
| 2014/0091230 | A1 | 4/2014 | Clark et al. |
| 2015/0231298 | A1* | 8/2015 | Eide .............. B01D 53/885 422/122 |
| 2018/0104375 | A1 | 4/2018 | Eide |
| 2018/0104376 | A1 | 4/2018 | Eide |
| 2018/0250431 | A1 | 9/2018 | Eide et al. |
| 2019/0216970 | A1 | 7/2019 | Eide et al. |
| 2021/0245100 | A1* | 8/2021 | Naito ............... B01D 53/885 |

FOREIGN PATENT DOCUMENTS

| | | | |
|---|---|---|---|
| JP | 11-114048 A | | 4/1999 |
| JP | 2000262605 | | 9/2000 |
| JP | 2003135973 | | 5/2003 |
| JP | 2003284926 | | 10/2003 |
| JP | 2003287354 | | 10/2003 |
| JP | 2006017358 | | 1/2006 |
| JP | 2007130042 | | 5/2007 |
| WO | WO2009038236 | | 3/2009 |
| WO | 2012/033818 | A1 | 3/2012 |
| WO | 2013/036553 | A2 | 3/2013 |
| WO | WO2016178698 | | 11/2016 |

OTHER PUBLICATIONS

International Preliminary Report on Patentability received for PCT Patent Application No. PCT/US2015/033364, mailed on Nov. 16, 2017, 15 pages.
Machine translation of JP 2003287354 (Year: 2003).
Supplementary European Search Report issued in PCT/US2015033364 dated Dec. 7, 2018.
U.S. Appl. No. 14/705,046, filed Jul. 18, 2017, Office Action.
U.S. Appl. No. 14/705,046, filed Nov. 13, 2017, Notice of Allowance.
International Search Report and Written Opinion received for PCT Patent Application No. PCT/US2020/045249, mailed on Oct. 22, 2020, 10 pages.
Office Action received for Chinese Patent Application No. 201580080274.9, mailed on Feb. 2, 2021, 7 pages (3 pages of English Translation and 4 pages of Original Document).
International Search Report of PCT/US2015/033364 (related application); Sep. 4, 2015.
U.S. Appl. No. 13/602,102, Mar. 11, 2014, Office Action.
U.S. Appl. No. 13/602,102, Oct. 9, 2014, Office Action.
U.S. Appl. No. 13/602,102, Apr. 9, 2015, Final Office Action.
U.S. Appl. No. 13/602,102, Nov. 12, 2015, Office Action.
U.S. Appl. No. 13/602,102, May 2, 2016, Final Office Action.
U.S. Appl. No. 13/602,102, Dec. 13, 2016, Notice of Allowance.
International Preliminary Report on Patentability received for PCT Patent Application No. PCT/US2020/045249, mailed on Feb. 17, 2022, 9 pages.
European Search Report received for EP Patent Application No. 20850911.7, mailed on Aug. 1, 2023, 7 pages.
Office Action received for Canadian Patent Application No. 3146108, mailed on May 18, 2023, 5 pages.
Office Action received for India Patent Application No. 202217011218, mailed on Aug. 29, 2022, 06 pages.
Office Action received for Chinese Patent Application No. 202080067889.9, mailed on Dec. 22, 2023, 10 pages.

* cited by examiner

PHOTOCATALYTIC OXIDATION DEVICE FOR TREATMENT OF AIR

CROSS-REFERENCE TO RELATED APPLICATIONS

This application claims priority to and the benefit of U.S. Provisional Patent Application No. 63/006,270, filed Apr. 7, 2020 and titled "Photocatalytic Oxidation Device for Treatment of Air," and U.S. Provisional Patent Application No. 62/883,410, filed Aug. 6, 2019 and titled "Photocatalytic Oxidation Device for In-Line Treatment of Air," the entirety of each being incorporated herein by this reference.

BACKGROUND

Conventional systems for treating ambient air and removing airborne particles include high-efficiency particulate air (HEPA) filtration systems. These systems utilize filters that are required to meet certain HEPA requirements, such as the ability to remove 99.97% of particles with diameter greater than or equal to 0.3 µm in air passing through the filter(s). While HEPA filtration systems may be useful for removing particles from the air, they suffer from all the limitations common to filtration systems, such as filters that clog over time and require continual monitoring and replacement. Filtration-based systems are also incapable of deactivating chemicals, removing unwanted gases, or removing smaller odor-causing molecules. Moreover, while a HEPA filtration system can remove several airborne contaminants, it will not treat nearby surface contaminants.

Other systems may utilize activated carbon filters or electrostatic filters. While these may be utilized to enhance the ability to trap contaminants and improve the effectiveness of filtration, they still involve the above-mentioned limitations common to filtration-based systems such as filter replacement, degrading filter performance over time, and the inability to treat surface contaminants.

Other air purification systems, commonly referred to as "ionizers," are designed to emit negative ions into the surrounding air. These ions attach to positively charged contaminants such as pollen and dust. The contaminants then become weighed down and are more likely to settle or are easier to trap in a collection plate. However, because many of the contaminants are simply moved to the floor or walls rather than destroyed or removed, they can reenter the air after the negative ions dissipate or disassociate. If a collection plate is used, it must be regularly cleaned or replaced as with any filtration system.

Other air purification systems are designed to use ultraviolet (UV) radiation to inactivate and/or degrade airborne contaminants. These systems may be referred to as UV germicidal irradiation or UVGI air purifiers. The UV light is typically tuned to short-wave UV light (UV-C light). In operation, air is directed through the system and past one or more UV lamps, with the intent of using the UV light to directly disinfect the passing air. Although UVGI systems are capable of destroying some contaminants rather than trapping/filtering all passing contaminants, they have limitations. For many bacteria and mold contaminants, especially spores, the brief exposure to UV light is not enough to effectively destroy the contaminant. Some volatile organic compounds (VOCs) may also be resistant to UV energy, or worse, be reactive with UV light in a way that makes them more harmful or exposed to nearby individuals.

Photocatalytic oxidation (PCO) air purifiers are somewhat similar to UV air purification systems in that they also utilize UV light. However, rather than using the UV light to directly interact with passing contaminants, PCO systems direct UV light onto a catalyst material. Water molecules in the ambient air then interact with the UV light and the catalyst to generate a variety of oxidizers such as hydroxyl radicals. The oxidizers can then attack organic molecule contaminants and degrade them into less harmful substances.

Thus, rather than trapping contaminants, PCO systems are capable of destroying and removing contaminants from the treated environment. However, conventional PCO systems have several limitations. For example, the passing air must be brought into sufficient proximity with the catalyst for the generated oxidizers to mix with the air and contact contaminants in the air. Ideally, a portion of the generated oxidizers should also continue to pass beyond the catalyst and UV lamp so that oxidizers can reach nearby surfaces and provide treatment of surface contaminants as well.

Several design decisions must therefore be made as to where to position the catalyst material and the UV assembly relative to each other and relative to the airflow path. If there is insufficient contact between passing air and the catalyst material, or if there is insufficient irradiation of the catalyst material, there will be reduced generation of oxidizers, poor mixing of the oxidizers with the air, or both, ultimately leading to suboptimal treatment of the contaminants. On the other hand, excessive contact between the catalyst and the airflow path and/or between the UV assembly and the airflow path may unnecessarily restrict airflow, which can increase the operational power demand needed to run the system and/or reduce the volumetric airflow through the system. Reduced airflow can hamper the treatment effectiveness of the system, increase the time it takes to clean the targeted environment, and/or hinder the ability of the system to emit oxidizers very far beyond the catalyst where they can treat surface contaminants.

Accordingly, there is an ongoing need for improved PCO air purification systems. An improved PCO air purification system would be structurally configured and dimensionally optimized to provide effective generation of oxidizers and effective mixing of the oxidizers with passing air while minimizing disruption to airflow.

SUMMARY

Described herein are PCO devices configured for enhanced performance in purifying ambient air. In one embodiment, a PCO device includes a frame, a pair of cell panels disposed opposite one another across the width of the frame, and a UV lamp disposed within an interior chamber defined by the frame and the cell panels. The cell panels include apertures that allow air to flow into and through the interior chamber. At least the interior surfaces and the aperture surfaces of the cell panels include a photocatalytic material such as a photocatalytic coating.

The PCO device is structurally configured and dimensionally optimized to provide effective irradiation of the photocatalyst, effective generation of oxidizers, and effective interaction between the airflow and the photocatalyst without overly restricting the airflow path. Embodiments described herein are capable of providing more effective purification of contaminants than conventional systems on a power basis (e.g., per watt used by the device), a per volume basis (e.g., per $cm^3$ taken up by the device), or both.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

BRIEF DESCRIPTION OF THE DRAWINGS

Various objects, features, characteristics, and advantages of the invention will become apparent and more readily appreciated from the following description of the embodiments, taken in conjunction with the accompanying drawings and the appended claims, all of which form a part of this specification. In the Drawings, like reference numerals may be utilized to designate corresponding or similar parts in the various Figures, and the various elements depicted are not necessarily drawn to scale, wherein:

DETAILED DESCRIPTION

Overview of Photocatalytic Oxidation Device

Figure 1:
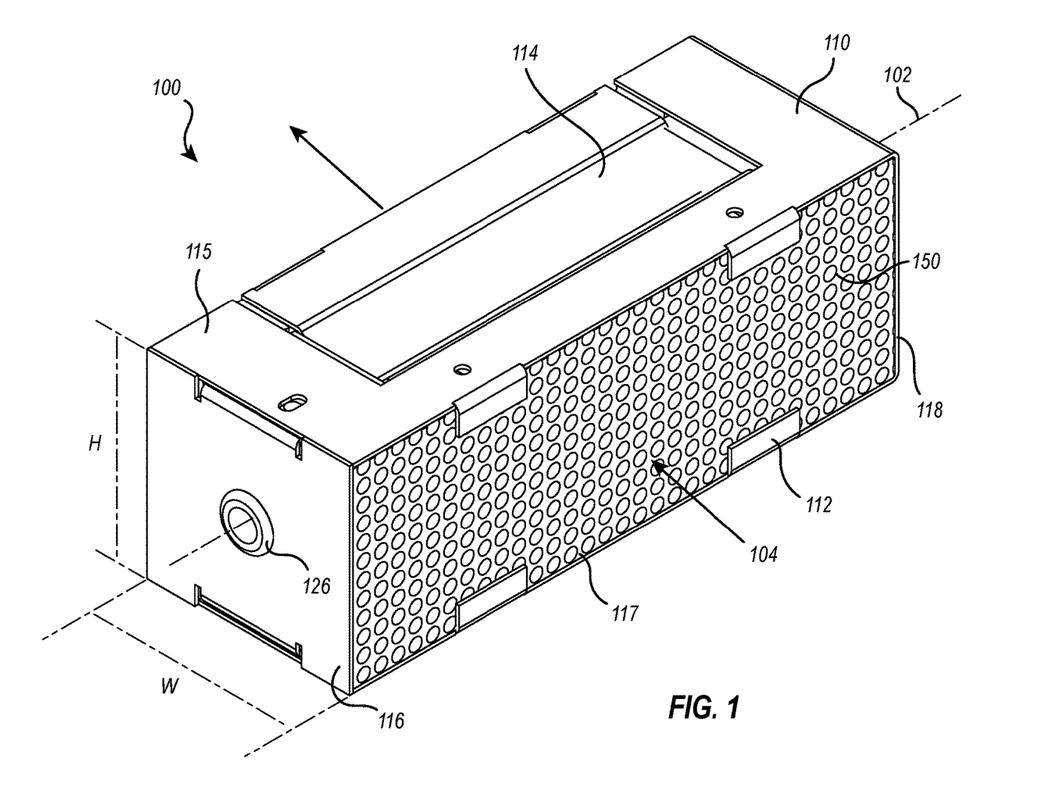
FIG. 1 illustrates an isometric view of an exemplary PCO unit.
Figure 2:
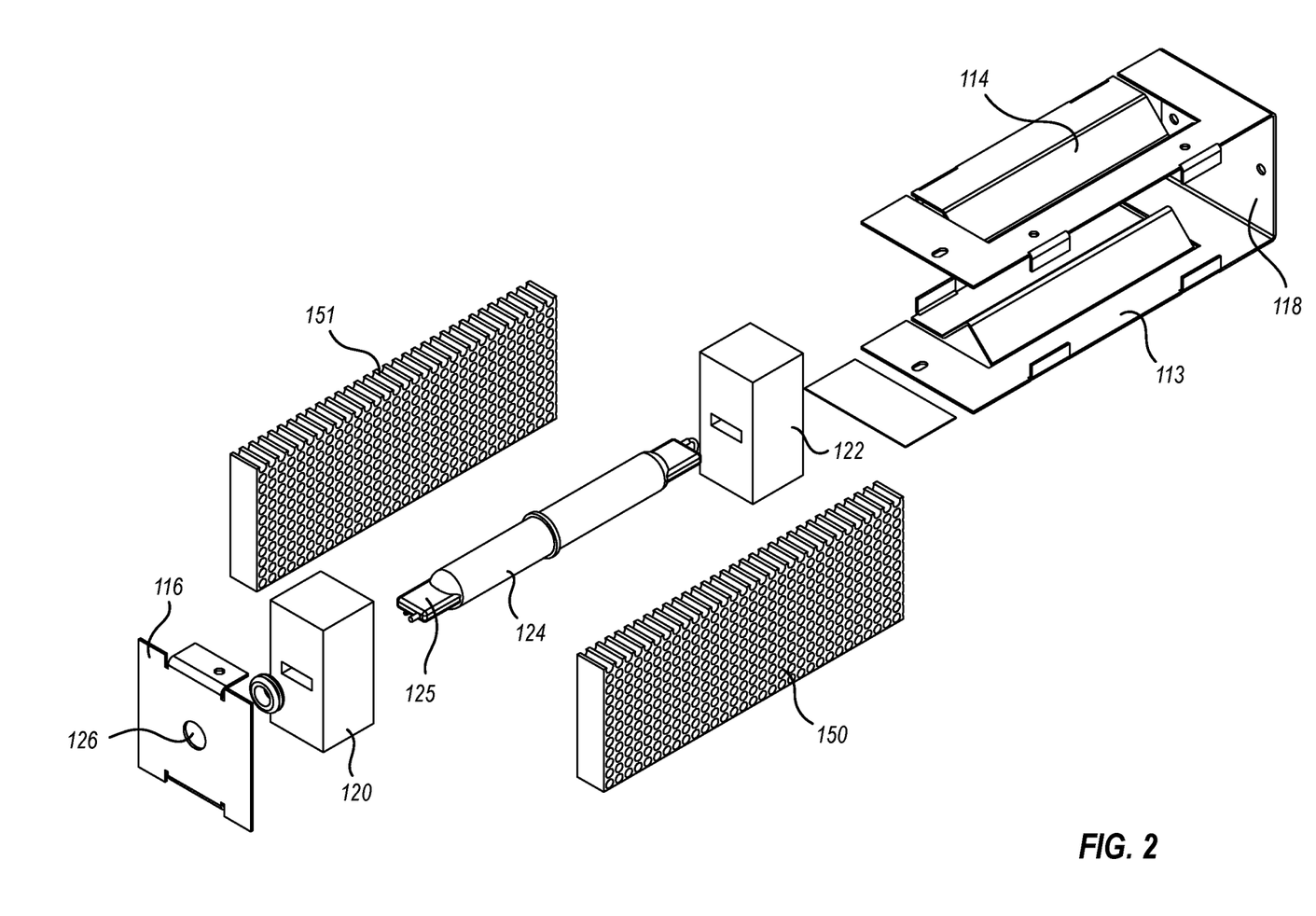
FIG. 2 illustrates the PCO unit in exploded view.

FIG. 1 illustrates an isometric view of an exemplary PCO unit 100 configured for inline placement within an airflow path, and FIG. 2 illustrates the PCO unit 100 in exploded view. The PCO unit 100 may be placed within the ductwork of a ventilation system, within a moveable air purification device, or be part of a larger air purification system having one or more additional air purification components, for example. Occasionally, for convenience, the PCO unit 100 will be referred to as the PCO device 100 or simply the unit 100 or the device 100.

The PCO unit 100 has a length that extends along a longitudinal axis 102, a height ("H"), and a width ("W"). In use, the unit 100 is oriented so that an airflow path 104 is substantially orthogonal to the longitudinal axis 102, allowing air to flow through the width of the device. For convenience in describing the unit 100, a "vertical" axis is taken to extend along the height of the device, and a "lateral" axis is taken to extend along the width of the device.

The descriptors "upper," "lower," "right," "left," "front," "back," "vertical," and "lateral" are used for convenience in describing the relative positions of the different components of the illustrated unit 100. However, it will be understood that the illustrated PCO unit 100 is not orientation dependent, and thus in some applications the "lower" side will not necessarily be facing in the direction of gravity, and the longitudinal axis 102 need not necessarily be orthogonal to the ground.

The illustrated PCO unit 100 includes a frame 110. The frame 110 forms an upper side 115, a lower side 117, a left/first laterally-extending side 116, and a right/second laterally-extending side 118. The frame 110 is configured to hold a front cell panel 150 and a preferably also a back cell panel 151 (see, e.g., FIG. 2). The longitudinally-extending cell panels 150 and 151 extend between the laterally-extending sides 116 and 118 and between the upper and lower sides 115 and 117 on opposite sides of one another. That is, one is positioned at the "front" of the device and one is positioned at the "back" of the device. In use, the cell panels 150 and 151 are intended to be oriented orthogonal to the airflow path 104. The left laterally-extending side 116 may include an access hole 126 for routing wires (such as electrical wires for the UV lamp 124) to/from the interior chamber of the device.

As shown, the frame 110 can be formed into a box shape where the laterally-extending edges of the upper side 115 and lower side 117 adjoin the corresponding laterally-extending edges of the laterally-extending sides 116 and 118, and where the longitudinally-extending edges of the upper side 115 and lower side 117 adjoin the corresponding longitudinally-extending edges of the cell panels 150 and 151. The frame 110 may also include one or more tabs 112 that aid in maintaining position of the cell panels 150 and 151. For example, one or more tabs may be connected to a longitudinally-extending edge of the upper side 115 and may extend a distance toward the lower side 117, and/or one or more tabs may be connected to a longitudinally-extending edge of the lower side 117 and may extend a distance toward the upper side 115.

The frame 110 may also include a reflector structure 114 (i.e., "reflective feature" or just "reflector") that extends longitudinally along a portion of the upper side 115. A similar reflector structure 113 may be included on the lower side 117 (see, e.g., FIG. 2). The reflector structure 114 protrudes inward toward the UV lamp within the interior chamber of the frame 110 and functions to better direct UV light onto the inner surfaces and apertures of the cell panels 150 and 151.

The reflectors 113 and 114 may have a "convex" cross-sectional shape (from the perspective of the interior chamber) such as the V-shaped cross-sectional shapes shown in the illustrated embodiment. The reflectors 113 and 114 are preferably positioned such that the most inwardly disposed "peaks" are aligned with and extend parallel to the UV lamp 124. The reflectors 113 and 114 are also preferably symmetrical about a vertical plane that lies on the longitudinal axis 102. Additional details regarding such reflector structures 114 are described in U.S. Pat. No. 9,867,897, which is incorporated herein by this reference. Further improvements to the reflectors 113 and 114, including how they are sized and positioned relative to other components of the PCO unit 100, are described in more detail below.

Referring to FIG. 2, the exploded view shows that one or more spacers, such as spacers 120 and 122, may be positioned within the interior chamber. The spacers 120 and 122 are configured to attach to the UV lamp 124 and to properly center the UV lamp within the interior chamber along the longitudinal axis 102. As shown, the spacers 120 and 122 are positioned adjacent the laterally-extending sides 116 and 118 of the frame 110, respectively, when the unit 100 is assembled.

In the illustrated embodiment, the UV lamp 124 includes terminal couplers 125 configured to insert within the corresponding spacers 120 and 122. A terminal coupler 125 may be provided at one or both ends of the UV lamp 124. The terminal couplers 125 include a non-circular profile sized to fit within corresponding slots within the spacers 120 and 122. The non-circular profile beneficially prevents rotation of the UV lamp 124. Electrical wires may be passed from the UV lamp 124, through the slot of the front spacer 120, and through the access hole 126.

Though the illustrated embodiment includes a single UV lamp 124, other embodiments may include multiple UV lamps. Multiple lamps may be stacked "vertically" within the interior chamber, with each parallel to the longitudinal axis 102, and/or may be positioned end to end along a direction parallel to the longitudinal axis 102, for example.

Additional Frame Details

Figure 3:
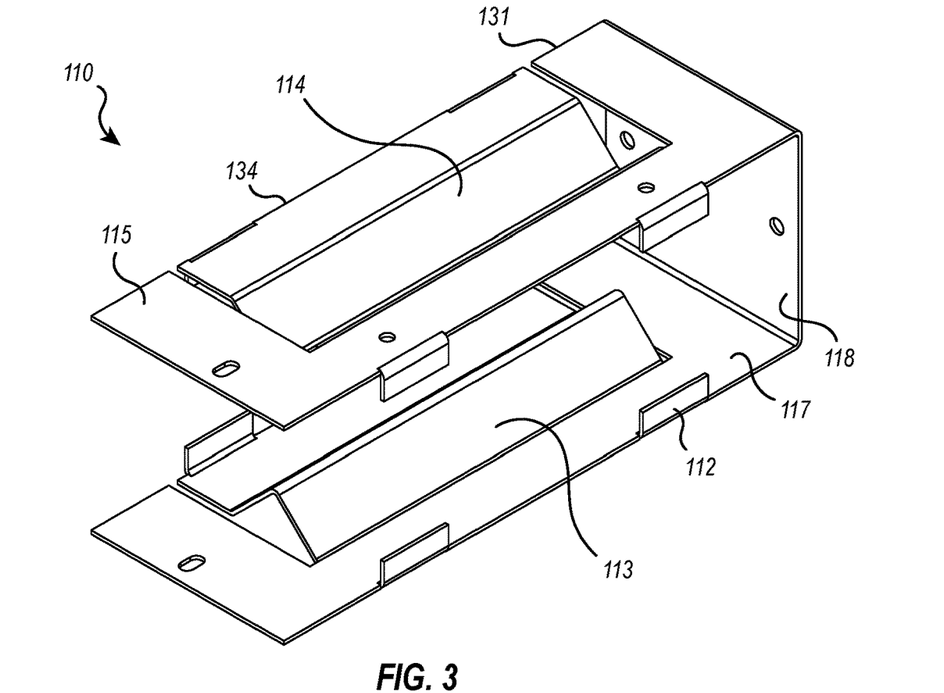
FIG. 3 illustrates a frame component of the PCO unit.

FIG. 3 illustrates a portion of the frame 110 where other components of the PCO unit 100 have been removed to better illustrate certain features of the frame 110. The frame 110 may include one or more holes 128 or other mounting features for receiving various fasteners, brackets, and/or other hardware known in the art for mounting or positioning the frame 110 at a desired location and orientation.

In the illustrated embodiment, the upper side 115, second laterally-extending side 118, and lower side 117 of the frame 110 are joined together as one contiguous piece. The first laterally-extending side 116 is formed as a separate piece that may be selectively attached to the upper side 115 and lower side 117 opposite the second laterally-extending side 118. This configuration provides several benefits to functionality and manufacturability of the device. For example, the spacers 120 and 122 and UV lamp 124 may be placed in their proper positions and then the cell panels 150 and 151 may be easily slid into place by inserting them in the front and sliding them toward the second laterally-extending side 118. Once in position, the first laterally-extending side 116 may be attached to hold the inserted features in place and finish the completed assembly.

The reflectors 113 and 114 may also be integrally formed as part of the same contiguous piece that forms the upper side 115, second laterally-extending side 118, and lower side 117 of the frame 110. In this configuration, a single sheet of flat stock material (e.g., aluminum, stainless steel, or other suitable metal) may be readily cut and bent/folded into the shape that forms the frame. For example, to form reflector 114, a pair of cuts 132 may be formed in the upper side 115 to allow bending of the portion of the upper side 115 that forms the reflector 114.

As shown, the cuts 132 may extend from the back edge 131 toward the front edge 130, but stop a distance before reaching the front edge 130, thereby allowing a portion of the back edge to be a free edge 134 that can be manipulated to allow bending and forming of the reflector 114. Alternatively, the cuts 132 could extend from the front edge 130 toward the back edge 132. Accordingly, the side from which the cuts 132 begin is not vital so long as a free edge is formed to allow bending of the portion of the upper side 115 disposed between the cuts 132.

The bottom reflector 113 may be formed in the same fashion as the upper reflector 114. The tabs 112 may also be integrally formed with the same contiguous piece of stock material used to form the other components of the portion of the frame 110 illustrated in FIG. 3. Accordingly, forming the frame 110 may be easily accomplished by cutting a common sheet of stock material to the appropriate size and shape, then bending it along the appropriate crease positions to form the frame 110. This can significantly reduce the number of manufacturing steps involved in forming the frame 110 while also providing a frame structure that readily lends itself to receiving and/or attaching to the other components required to complete the full assembly of the device.

Operation of the Photocatalytic Oxidation Unit

In operation, the device is positioned in line with an airflow path. The UV lamp 124 is energized and emits UV radiation toward catalytic surfaces of the cell panels 150 and 151, thereby generating oxidizers. The oxidizers are then mixed with the passing air and preferably at least some of the oxidizers pass out of and beyond the unit 100 with the passing air.

Figure 4:
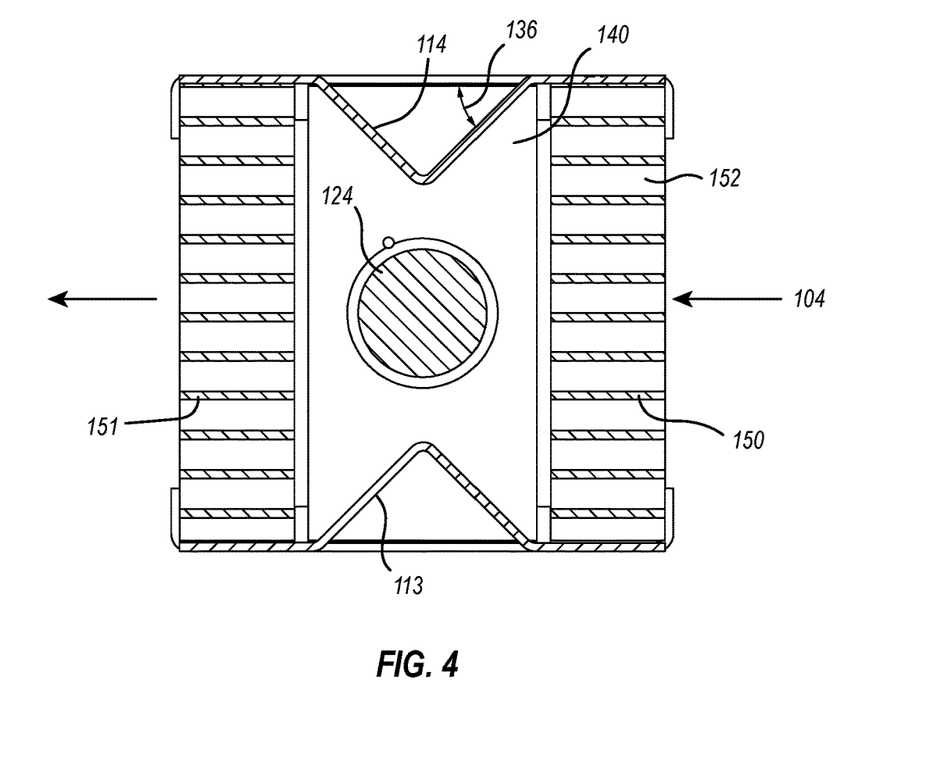
FIG. 4 illustrates a cross-sectional view of the PCO unit along a vertical plane orthogonal to the longitudinal axis.

FIG. 4 is a cross-sectional view of the PCO unit 100 with a cross section taken along a plane orthogonal to the longitudinal axis 102 of the device. As air flows toward the device along the airflow path 104, it will first reach the front cell panel 150. After passing through the apertures 152 of the front cell panel 150, the air will then pass into and through the interior chamber 140. The air will then pass through the apertures 152 of the back cell panel 151 to move beyond the PCO unit 100 and into the targeted environment.

The cell panels 150 and 151 include a photocatalyst coating. The photocatalyst coating is placed at least on the inside surfaces of the cell panels 150 and 151 facing the UV lamp 124. Preferably, the photocatalyst coating also extends into the apertures 152 to coat the surfaces of the apertures 152. The photocatalyst coating may comprise a metal oxide such as titanium oxide and may optionally include one or more transition metals and/or alloys of transition metals. Examples of additional or alternative photocatalytic materials that may be utilized in the coating include graphene oxide, metal-organic frameworks (MOFs), other semiconductor materials, quantum dots, tantalite, other oxides (e.g., zinc, copper, iron, cadmium, tin, zirconium, or gallium oxide), sulfides (e.g., zinc sulfide), silica, and combinations thereof As shown in the cross-sectional view of FIG. 4, the reflectors 113 and 114 are positioned to reflect light toward the inner surfaces and apertures 152 of the cell panels 150 and 151. The reflectors 113 and 114 are configured with angle 136 set to optimize the amount of light reflected back toward the cell panels 150 and 151 rather than to other portions of the interior chamber 140. Effective results have been achieved by setting angle 136 at about 30° to about 60°, or more preferably about 40° to about 50°, such as about 45°. The opposite angle is preferably also substantially equal such that the reflector is symmetrical about a plane extending through the longitudinal axis.

Figure 7:
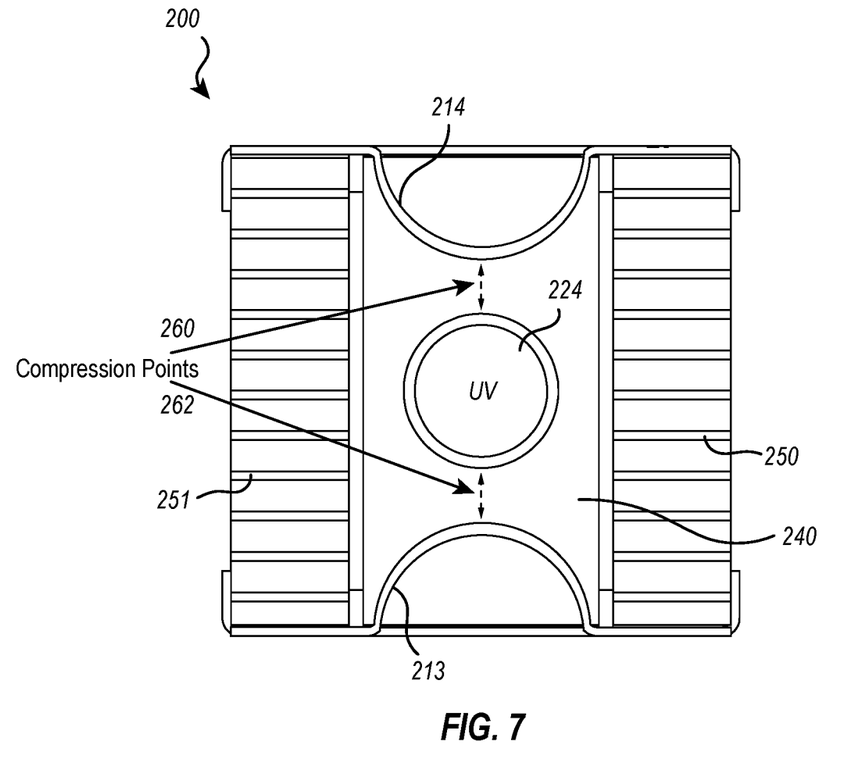
FIG. 7 illustrates a cross-sectional view of another embodiment of a PCO unit along a vertical plane orthogonal to the longitudinal axis, the illustrated PCO unit including reflectors having a curved cross-sectional shape.
Figure 9:
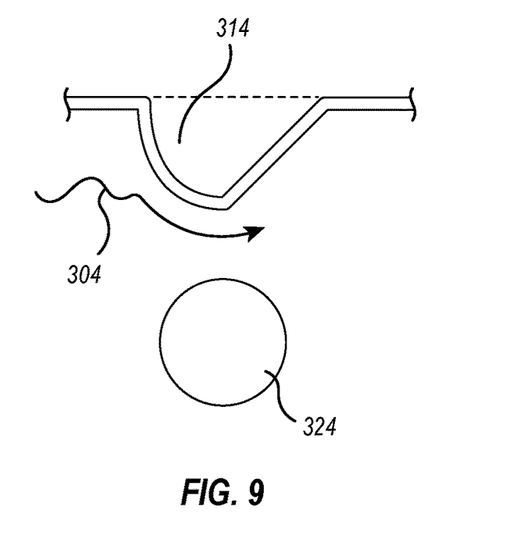
FIGS. 9 and 10 illustrate alternative embodiments of reflectors having different cross-sectional shapes.
Figure 10:
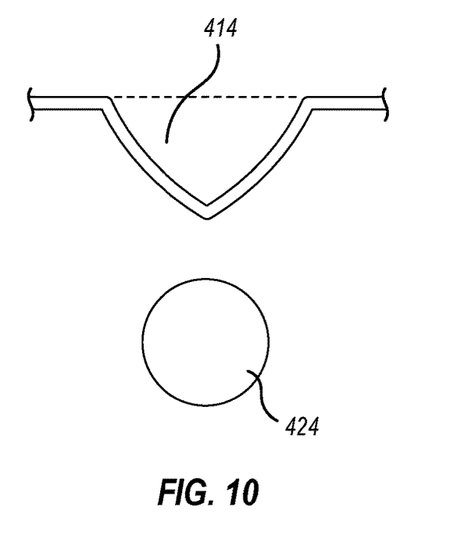

The embodiment illustrated in FIG. 4 shows reflectors that are "V" shaped in cross section. Other reflector embodiments may have other shapes, such as curved, semicircle shapes in cross section (e.g., as shown in FIG. 7), a combination or hybrid between a V and a semicircle in cross section (e.g., as shown in FIG. 10), other curved shapes (e.g., that are not necessarily circular in cross section), or a shape where a portion is flat/angled and another portion is curved (e.g., as shown in FIG. 9), for example.

The apertures 152 are illustrated here as being substantially horizontal (i.e., substantially perpendicular to the inner surface of the cell panel). In other embodiments, one or more of the apertures may be angled, such as by about 25° to about 65° from the inner surface of the cell panel. Angled apertures are described in more detain in U.S. Pat. No. 9,867,897, which has been incorporated herein.

Oxidizers generated during operation of the device may include, for example, hydrogen peroxides, hydroxides, free oxygen molecules, super oxide ions, and ozone. Preferably, however, the PCO unit 100 is configured so that ozone generation is limited or eliminated. While ozone is a powerful oxidizing agent, excess ozone may cause respiratory irritation in sensitive individuals. It has been found that by tailoring the PCO unit 100 to generate effective levels of oxidizers while minimizing or eliminating ozone, effective purification performance is maintained without the potential detrimental effects related to excess ozone. In order to provide these performance characteristics, the UV lamp 124 preferably emits light with a wavelength of about 185 to 254 nm. The UV lamp 124 will typically be rated at about 5 to 30 watts.

Optimization of Airflow and Photocatalytic Activity

The structural configuration of the PCO unit 100 is designed to provide effective photocatalytic activity, effective interaction between the airflow and the generated oxidizers, and effective overall volumetric airflow. These functions interact with one other, and enhancing one of these functions may involve tradeoffs with one or more of the other functions.

For example, photocatalytic activity may be enhanced by increasing the overall surface area of the UV lamp(s) (e.g., using a bigger lamp) and/or by increasing the proportion of photocatalytic material within the airflow path. However, either of these changes will also likely increase the airflow resistance of the device, thus lowering the volumetric airflow or requiring more power to maintain higher pressures across the device. When airflow through the PCO unit 100 is restricted, the air turnover rate for a given room/environment is reduced, meaning it takes longer to purify the air or meaning more purification units are required. Lower airflow also limits the distance the generated oxidizers can reach beyond the unit 100, thus limiting the surfaces that can be treated with the unit 100.

Similarly, airflow may be increased by limiting the contact between the air and the photocatalytic material, such as by simply passing the air over a photocatalyst rather than through multiple apertures or by increasing the size of the apertures. However, this limits the interaction between the air and the generated oxidizers, which limits the mixing and distribution of the oxidizers within the air. For a given level of generated oxidizers, the oxidizers are therefore less likely to contact and treat the contaminants. Likewise, airflow may be increased by enlarging the spacing between the UV lamp and the photocatalytic material, by reducing or eliminating the reflectors 113 and 114, and/or by reducing the overall surface area of the UV lamp, but this tends to lower the overall photocatalytic generation of oxidizers.

Figure 5:
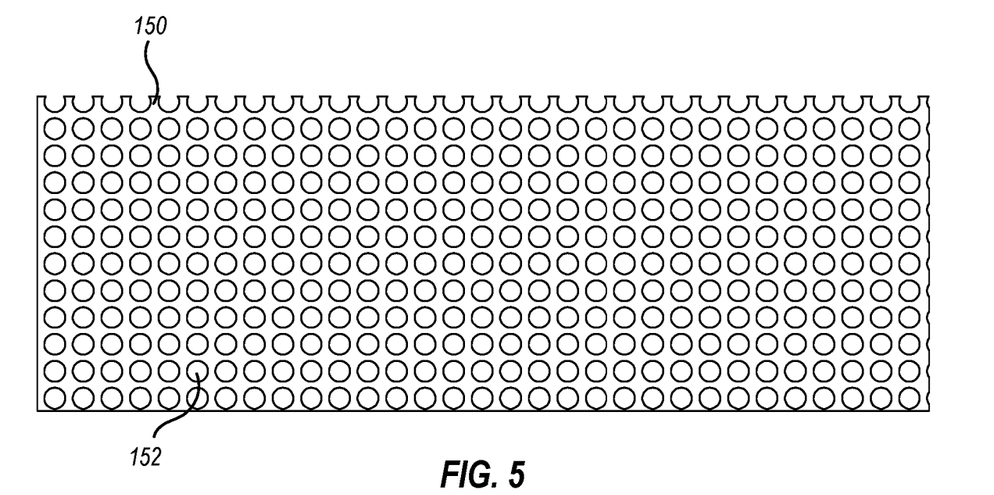
FIG. 5 illustrates a front view of a photocatalytic cell panel with apertures.

FIG. 5 illustrates a front view of the cell panel 150, showing the spacing and distribution of apertures 152. This is the surface that the airflow "sees" as it moves along the airflow path 104 and initially reaches the device 100. Accordingly, smaller apertures will tend to restrict airflow to a greater degree than larger apertures. However, because the coated inner surfaces of the apertures 152 provides a significant portion of the photocatalytic activity of the device, and because smaller apertures allow for a greater overall area of active photocatalytic surfaces, smaller apertures tend to provide greater photocatalytic activity.

It has been found that setting the average cross-sectional area of each aperture 152 at greater than about 5 mm² but less than about 45 mm² provides effective photocatalytic activity without overly restricting airflow. The apertures 152 may more preferably be sized with an average cross-sectional area of about 6 mm² to about 40 mm², or about 7 mm² to about 30 mm², or about 8 mm² to about 20 mm², or about 9 mm² to about 15 mm². Apertures 152 that are too small tend to reduce overall performance of the device by overly restricting airflow, while apertures 152 that are too large tend to reduce overall performance of the device by overly limiting photocatalytic activity.

The number of apertures 152 included in the cell panel 150 may be varied. Preferably, apertures 152 are provided at a number such that about 25% to about 75% of the cross-sectional area of the cell panel 150 is made up of the apertures 152, or more preferably about 35% to about 65%, or about 40% to about 60% of the cross-sectional area of the cell panel 150 is made up of the apertures 152, with the cross-section being taken along a plane that lies along the vertical and longitudinal axes (e.g., giving the view shown in FIG. 5).

Accordingly, the device 100 has been found to provide enhanced overall performance when the apertures are sized within the foregoing ranges and are provided within the foregoing amounts. The term "enhanced overall performance," as used herein, means the ability to better remove contaminants from a given room/environment on a power basis (e.g., per watt used by the device), a per volume basis (e.g., per cm³ taken up by the device), or both, as compared to a device not having the same dimensional optimization.

Figure 6:
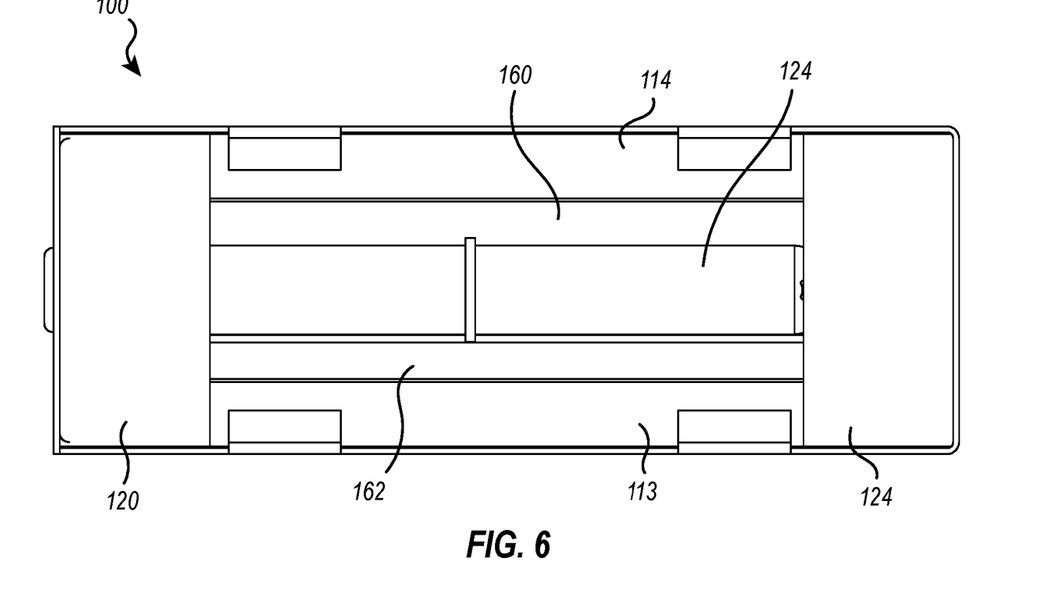
FIG. 6 illustrates a cross-sectional view of the PCO unit along a vertical plane aligned with the longitudinal axis

FIG. 6 illustrates a front view of the PCO unit 100 with cell panels 150 and 151 removed, showing the UV lamp 124, spacers 120 and 122, and reflectors 113 and 114. These are the surfaces that the airflow "sees" as it moves past the front cell panel 150 and initially enters the interior chamber 140. As shown, the airflow path is blocked by these components and passes through a pair of gaps 160 and 162 disposed between the UV lamp 124 and the reflectors 113 and 114.

The size of the gaps 160 and 162 through the cross-sectional area affects the volumetric airflow through the device 100 and the photocatalytic activity of the device 100. Increasing the size of the gaps 160 and 162 allows greater airflow but tends to lower photocatalytic activity (such as by moving the reflectors 113 and 114 farther from the UV lamp 124). On the other hand, reducing the gaps 160 and 162 (such as by moving the reflectors 113 and 114 closer to the UV lamp 124) may increase photocatalytic activity but will cause a greater restriction of airflow.

It has been found that optimizing the gap size, reflector size, and UV lamp size relative to each other can provide for greater overall performance of the device. A "gap fraction" is defined herein as the fraction of the cross-sectional area of the device 100 within the gaps 160 and 162, with the cross-section being taken along a plane that lies along the vertical and longitudinal axes (e.g., giving the view shown in FIG. 6). In some embodiments, the device 100 is configured with a gap fraction of about 0.1 to about 0.5, or more preferably with a gap fraction of about 0.125 to about 0.4, or even more preferably about 0.15 to about 0.3 or about 0.15 to about 0.2.

Referring back to FIG. 4, the width of the cell panels 150 and 152 may also be varied. Wider cell panels provide longer apertures 152 with greater overall surface area, and thus provide greater photocatalytic activity, but also increase the length through which the air must pass through the apertures and thus increases airflow resistance.

A "cell fraction" is defined herein as the combined width of the cell panels 150 and 152 divided by the overall width between the cell panels 150 and 152 (from outer surface to outer surface). The device 100 may be configured with a cell fraction of about 0.2 to about 0.7, more preferably about 0.3 to about 0.6, and even more preferably about 0.4 to about 0.5. Setting the cell fraction within the foregoing ranges was found to provide improved overall performance of the device 100.

Still referring to FIG. 4, the distance between the UV lamp 124 and the inner surfaces of the cell panels 150 and 152 may also be varied. A greater width between the UV lamp 124 and the cell panels 150 and 152 allows greater residence time for air passing through the interior chamber 140, but also reduces the photocatalytic activity by increasing the distance between the lamp 124 and the cell panels 150 and 152.

A "light fraction" is defined herein as the width/diameter of the UV lamp 124 divided by the overall width between inner surfaces of the opposing cell panels 150 and 152. The device 100 may be configured with a light fraction of about 0.45 to about 0.7, or more preferably about 0.5 to about 0.6. Setting the device 100 so that the light fraction was within the foregoing ranges was found to provide improved overall performance of the device 100.

The following description provides some dimensions of an exemplary PCO unit 100 that has been found to provide effective performance in several applications, particularly in applications involving modular, moveable room cleaning units with integrated fan assembly. It will be understood, however, that the exemplary dimensions are not necessarily limiting, and that other embodiments may be resized or scaled to provide particular application needs.

In one embodiment, the device 100 may have an overall height of about 1.5 to 2.5 inches (about 3.8 cm to 6.4), an overall width of about 1.5 to 2.5 inches (about 3.8 to 6.4 cm), and a length of about 4 to 8 inches (about 10 to 20 cm). The cell panel may be sized to fit accordingly, and may have a width of about 5 mm to about 30 mm, or more preferably about 10 mm to about 20 mm, or even more preferably about 10 mm to about 15 mm. The UV lamp 124 may also be sized accordingly to fit within the overall dimensions of the device 100, and thus may have a length of about 3 to 7 inches (about 8 to 18 cm), and a diameter of about 0.25 inches to about 0.75 inches (about 0.6 to 2 cm). The reflectors 113 and 114 may be sized so as to extend inward from the respective lower and upper surfaces 117 and 115 a distance of about 0.25 inches to about 0.75 inches (about 0.6 to 2 cm).

Additional Features of the Reflectors

The photocatalytic oxidation device embodiment described above includes reflectors 113 and 114 that are "V" shaped in cross section (see, e.g., FIG. 4). In other embodiments, one or both of the reflectors may have a different shape. FIG. 7 illustrates a cross-sectional view (taken along a plane orthogonal to the longitudinal axis) of an embodiment of a photocatalytic oxidation device 200 that includes reflectors 213 and 214, a UV lamp 224, cell panels 250 and 251, and an interior chamber 240. The embodiments shown in FIGS. 7-11 may be configured with features and dimensions similar to the photocatalytic oxidation device 100 described above, and the above description is therefore also applicable to any embodiments that include features described in relation to FIGS. 7-11, except where such features are specifically described as different.

As shown, the reflectors 213 and 214 have a semicircular shape in cross section. That is, the cross-sectional shape of the reflectors 213 and 214 omits any corners or edges. The reflectors 213 and 214 beneficially minimize disturbance to passing air and thereby minimizes the introduction of turbulence in the passing air. Air passing through the interior chamber 240 will pass through gaps 260 and 262, which act as compression points. The air velocity increases as the air moves through the gaps 260 and 262.

The curved surfaces of the reflectors 213 and 214 beneficially allow for smooth airflow through the gaps 260 and 262 while minimizing the formation of turbulence as compared to airflow across reflectors with angled faces, corners, and/or edges. Excess turbulence may be undesirable because it disrupts airflow and reduces the amount of air coming out of the device 200, and less air passing out of the device 200 means reduced delivery of generated oxidizers to the surrounding environment.

Figures 8A, 8B:
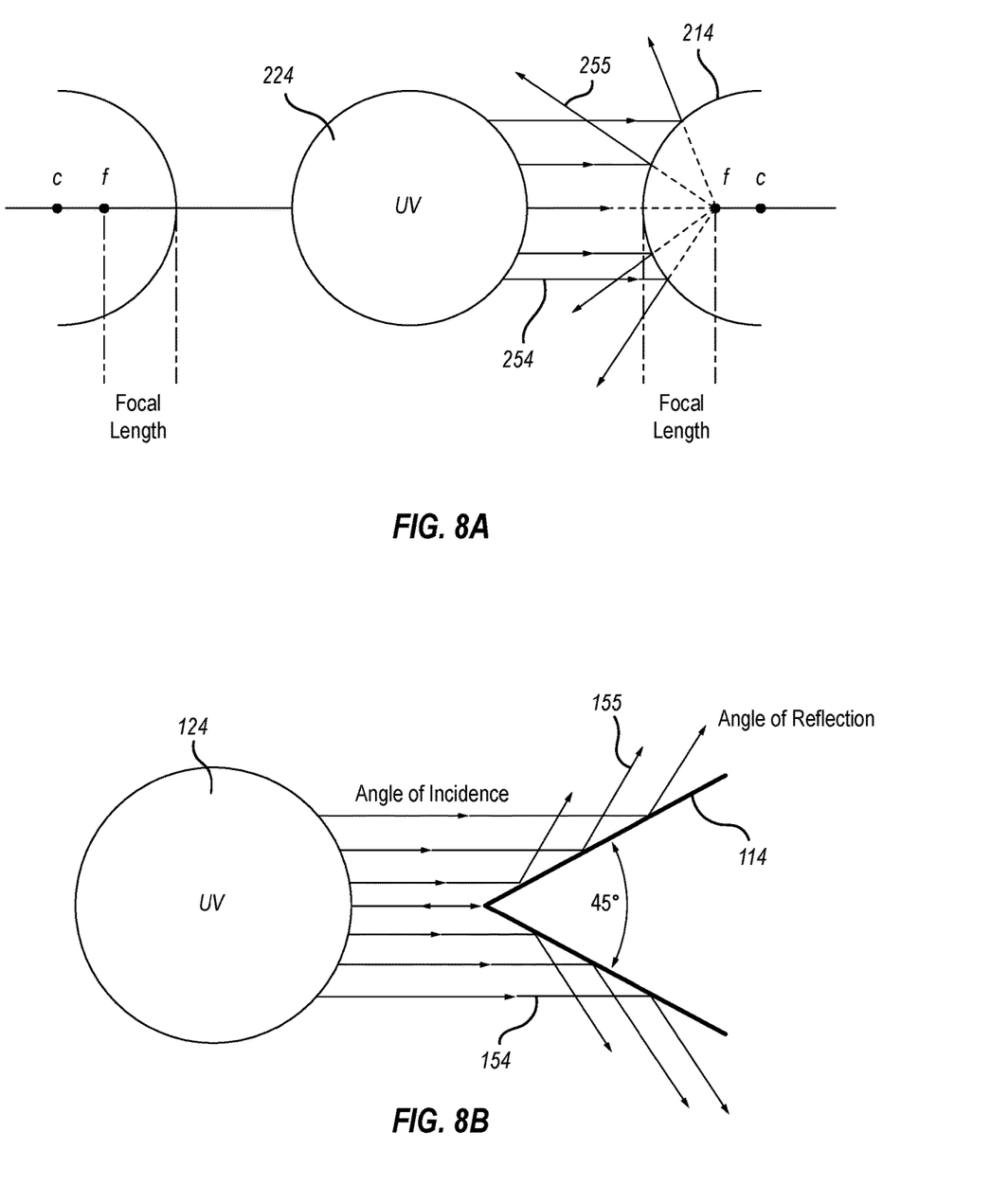
FIGS. 8A and 8B illustrate different light reflection patterns of the curved reflectors and angled reflectors.

FIG. 8A illustrates the reflective pattern where a semicircle-shaped reflector is utilized. As light rays 254 are directed to the reflector 214, reflected rays 255 reflect from the reflector 214 in alignment with the focal point. The focal point is typically located about half of the distance between the center of curvature and the pole of the reflector 214, which in this arrangement is typically the point of the reflector 214 closest to the UV lamp 224. As shown, most of the reflected rays 255 will be directed back inward in a direction facing toward the cell panels. This is beneficial because increasing the amount of incident light upon the photocatalytic surfaces of the cell panels increases the generation of oxidizers and therefore increases the overall photocatalytic activity of the device.

In contrast to the reflection pattern of the reflector 214 shown in FIG. 8A, the angled reflector 114 shown in FIG. 8B has a reflection pattern that is typically less desirable. As light rays 154 are directed from the UV lamp 124 toward the reflector 114, the reflected rays 155 will reflect outward from the surface of the reflector 114 with an angle of reflection that is equal to the angle of incidence. This means that most of the reflected rays will be directed somewhat outward rather than inward toward the center of the cell panels.

The reflectors may have shapes other than the V shape or the semicircle shape. In some embodiments, for example, a reflector may have a shape that is asymmetric in cross section. FIG. 9 illustrates one example of a UV lamp 324 associated with a reflector 314 that is asymmetrical in cross section. The reflector 314 may be shaped so that a front portion has a greater curvature than a back portion. For example, the front portion may have a shape that generally follows the contours of a semicircle, while the back portion has a flat face similar to the back portion of a V-shaped embodiment. Air flowing through the device in the direction indicated by arrow 304 will first contact the curved, front portion of the reflector 314. An asymmetrical reflector such as the illustrated reflector 314 is useful where minimization of turbulence is desired but where the reflective pattern of a flat surface is desired for the back portion of the reflector 314. The curved, front portion of the reflector 314 can aid in minimizing the generation of turbulence, while the flat, back portion of the reflector 314 can provide a standard, flat surface reflective pattern.

FIG. 10 shows another example where a reflector 414 has a cross-sectional shape somewhere between a V shape and a semicircle. For example, though the reflector 414 has a recognizable apex at the point closest to the UV lamp 424, the sides extending from the apex have a slightly convex curvature rather than the straight, flat shape of a V-shaped embodiment. A reflector such as reflector 414 can provide intermediate effects that are between a V-shaped embodiment and a semicircle embodiment. Such embodiments may be useful, for example, in applications where it is desirable to balance the effects of a semicircle shape (such as reducing turbulence) with the effects of a V shape (such as providing simpler reflective patterns).

Various gradations between a semicircle shape and a V shape may be selected based on particular application needs. For example, if a semicircle-shaped reflector has a curvature (the reciprocal of the radius) of some value X, and each of the "legs" of a similarly sized V-shaped reflector have a curvature of 0, a reflector may be configured with legs having any curvature that is a fraction of X. Some embodiments, for example, may include a reflector with legs having a curvature that is 10%, 20%, 30%, 40%, 50%, 60%, 70%, 80%, or 90% of X. Each leg may have the same or different curvature. As an example, the curvature of a semicircle-shaped reflector may be about 0.1625 inches to about 1 inch, or about 0.25 inches to 0.75 inches, or about 0.35 inches to about 0.6 inches. In other words, "X" may be equal to about 0.1625 inches to about 1 inch, or about 0.25 inches to 0.75 inches, or about 0.35 inches to about 0.6 inches.

Figure 11:
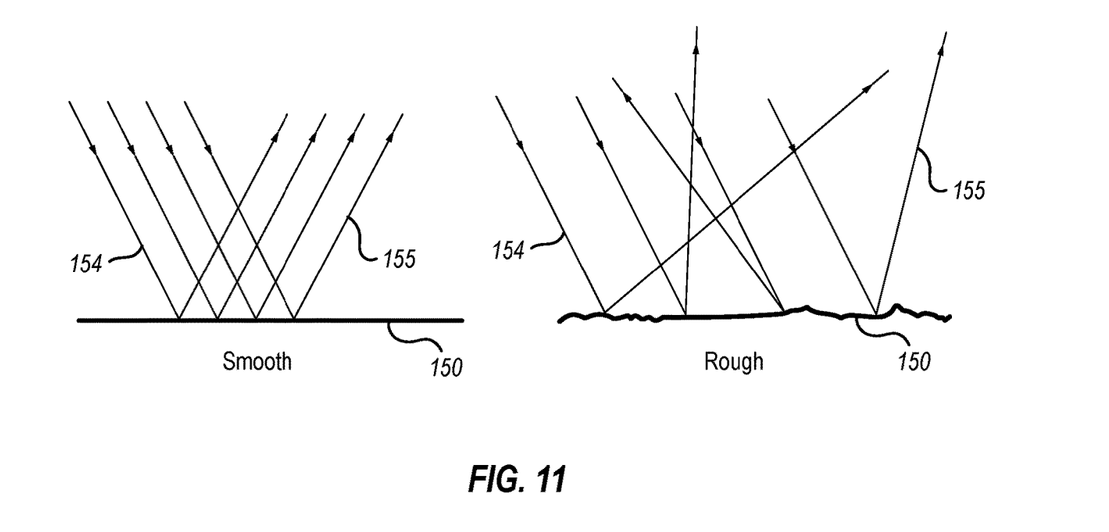
FIG. 11 schematically illustrates different reflective features of surfaces having different roughness.

FIG. 11 schematically illustrates surface features of the reflectors, and how differences in surface smoothness/roughness can affect the reflection pattern. As shown, where the reflector surface 150 is rough, projected light rays 154 are reflected somewhat erratically. In contrast, where the surface 150 is smooth, the reflected light rays 155 are more uniform and more consistently aligned in the intended direction of reflection. A smooth, highly reflective surface provides increased and more consistent light rays toward the photocatalytic coating of the cell panels. The reflectors described herein are therefore preferably made from polished aluminum or another highly reflective and smooth surface. For example, the surface of the reflector preferably has a glossiness of at least about 50 GU (gloss units), or at least about 70 GU, or at least about 90 GU, or at least about 110 GU, or at least about 130 GU, or at least about 150 GU, when measured at 20, 60, or 85 degrees.

Reflectors described herein may additionally or alternatively include one or more films and/or coatings for enhancing reflectivity/glossiness. A film and/or coating may be formed from a suitable polymer material. Examples include polyester materials such as polyethylene materials (e.g., polyethylene terephthalate (PET)). A particularly suitable example is biaxially-oriented PET (BoPET), such as the BoPET materials sold under the trade name Mylar®. The films and/or coatings may be aluminized so as to have a shiny, reflective surface.

In one example, a reflector made from a standard aluminum sheet material was able to reflect about 93% of the UV light in the 185 to 254 nm range. Polishing the aluminum enhanced reflection to 95%. The addition of an aluminized BoPET film applied over the unpolished aluminum provides about 98% reflection.

Conclusion

While certain embodiments of the present disclosure have been described in detail, with reference to specific configurations, parameters, components, elements, etcetera, the descriptions are illustrative and are not to be construed as limiting the scope of the claimed invention.

Furthermore, it should be understood that for any given element of component of a described embodiment, any of the possible alternatives listed for that element or component may generally be used individually or in combination with one another, unless implicitly or explicitly stated otherwise.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, or less than 1% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "widget") may also include two or more such referents.

It will also be appreciated that embodiments described herein may include properties, features (e.g., ingredients, components, members, elements, parts, and/or portions) described in other embodiments described herein. Accordingly, the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features.

The invention claimed is:

1. A photocatalytic oxidation device, comprising:
   a frame having a length, width, and height, with a longitudinal axis extending through the length of the frame;
   a pair of cell panels disposed opposite one another across the width of the frame, an interior portion of the frame between the cell panels defining an interior chamber, the cell panels including a plurality of apertures to allow air to flow into and through the interior chamber, and at least interior surfaces of the cell panels and aperture surfaces of the cell panels including a photocatalytic material; and
   an ultraviolet lamp disposed within the interior chamber and extending along the longitudinal axis,
   wherein a cell fraction is equal to a combined width of the cell panels divided by a width between outer surfaces of the cell panels, and wherein the cell fraction is about 0.2 to about 0.7.

2. The device of claim 1, wherein the cell fraction is about 0.3 to about 0.6.

3. The device of claim 2, wherein the cell fraction is about 0.4 to about 0.5.

4. The device of claim 1, wherein the frame further comprises one or more tabs each disposed adjacent to one of the cell panels and configured to aid in maintaining position of the respective cell panel.

5. The device of claim 1, the frame further comprising one or more reflectors extending into the interior chamber toward the ultraviolet lamp.

6. The device of claim 5, wherein the one or more reflectors extend parallel to the longitudinal axis.

7. The device of claim 5, wherein an inward-most portion of the one or more reflectors also extends parallel to the longitudinal axis and is aligned with the ultraviolet lamp.

8. The device of claim 5, wherein the one or more reflectors are symmetrical about a vertical plane that lies on the longitudinal axis.

9. The device of claim 5, wherein the one or more reflectors have a V-shaped cross section, a semicircle-shaped cross section, or a curved shape between a V-shape and a semicircle in cross section.

10. The device of claim 1, wherein the frame includes first and second laterally-extending sides opposite one another, wherein the cell panels form a front side and a back side, wherein the upper side, second laterally-extending side, and bottom side form a single, contiguous section of material, and wherein the first laterally-extending side is selectively attachable to the single, contiguous section of material.

11. The device of claim 1, wherein the apertures of the cell panels extend in a direction that is orthogonal to the longitudinal axis.

12. The device of claim 1, wherein the average cross-sectional area of the apertures is about 5 mm$^2$ to about 45 mm$^2$.

13. The device of claim 1, wherein the apertures are included in an amount such that about 25% to about 75% of the cross-sectional area of the cell panels are made up of the apertures.

14. The device of claim 1, wherein a light fraction is equal to a diameter of the ultraviolet lamp divided by a width between inner surfaces of the cell panels, and wherein the light fraction is about 0.45 to about 0.7.

* * * * *